(12) United States Patent
Martinez (10) Patent No.: US 7,573,577 B2
(45) Date of Patent: Aug. 11, 2009

(54) SPATIAL HETERODYNE WIDE-FIELD COHERENT ANTI-STOKES RAMAN SPECTROMICROSCOPY

(75) Inventor: Robert E. Martinez, Providence, RI (US)

(73) Assignee: Southwest Research Institute, San Antonio, TX (US)

( * ) Notice: Subject to any disclaimer, the term of this patent is extended or adjusted under 35 U.S.C. 154(b) by 185 days.

(21) Appl. No.: 11/551,029

(22) Filed: Oct. 19, 2006

(65) Prior Publication Data
US 2007/0121119 A1 May 31, 2007

Related U.S. Application Data

(60) Provisional application No. 60/729,015, filed on Oct. 21, 2005.

(51) Int. Cl.
*G01B 9/02* (2006.01)
*G01J 3/44* (2006.01)
(52) U.S. Cl. ...................... 356/451; 356/301
(58) Field of Classification Search ................. 356/301, 356/451
See application file for complete search history.

(56) References Cited

U.S. PATENT DOCUMENTS 4,405,237 A 9/1983 Manuccia et al. ........... 356/301
5,671,085 A 9/1997 Gustafsson et al. ......... 359/385
6,798,507 B2 9/2004 Xie et al. .................... 356/301

OTHER PUBLICATIONS

Bailey et al.; "Enhancement of axial resolution in fluorescence microscopy by standing-wave excitation," *Nature*; 366:44-48, 1993.
Cheng and Xie, "Coherent anti-Stokes Raman scattering microscopy: instrumentation, theory and applications," *J. Phys. Chem. B.*, 108:827-840, 2004.
Duncan et al., "Scanning coherent anti-Stokes Raman microscope," *Opt. Lett.*, 7:350-352, 1982.
Frohn et al., "True optical resolution beyond the Rayleigh limit achieved by standing wave illumination," *Proc. Natl. Acad. Sci. USA*, 97:7232-7236, 2000.
Gustafsson et al., "$I^5M$: 3D widefield light microscopy with better than 100 nm axial resolution," *J. Microscopy*, 195:10-16, 1999.
Gustafsson et al., "Sevenfold improvement of axial resolution in 3D widefield microscopy using two objective lenses," *SPIE*; 2412:147-156, 1995.
Gustafsson, "Extended resolution fluorescence microscopy," *Curr. Opinion. Struct. Bio.*, 9:627-634, 1999.
Gustafsson, "Surpassing the lateral resolution limit by a factor of two using structured illumination microscopy," *J. Microscopy*, 198:82-87; 2000.

(Continued)

*Primary Examiner*—Hwa S Lee (Andrew)
(74) *Attorney, Agent, or Firm*—Grossman Tucker et al (57) ABSTRACT

Methods for chemically-resolved optical microscopy are presented. The methods can provide a wide-field, spatial interference imaging using multiple nonlinear scattering channels to produce multiple, spatially coherent anti-Stokes Raman scattering (CARS).

17 Claims, 7 Drawing Sheets

OTHER PUBLICATIONS

Hashimoto and Araki, "Three-dimensional transfer functions of coherent anti-Stokes Raman scattering microscopy," *J. Opt. Soc. Am. A. Opt. Image Sci. Vis.*, 18:771-776, 2001.

Heinrich et al., "Wide-field coherent anti-Stokes Raman scattering microscopy," *App. Phys. Lett.*, 94:816-818, 2004.

Holtom et al., "Achieving molecular selectivity in imaging using multiphoton Raman spectroscopy techniques," *Traffic*, 2:781-788, 2001.

Kee and Cicerone, "Simple approach to one-laser, broadband coherent anti-Stokes Raman scattering microscopy," *Opt. Lett.*, 29:2701-2703, 2004.

Potma et al., "Nonlinear coherent four-wave mixing in optical microscopy," *J. Opt. Soc. Am. B.*; 17:1678-1684, 2000.

Potma et al., "Real-time visualization of intracellular hydrodynamics in single living cells," *Proc. Natl. Acad. Sci. USA*, 98:1577-1582, 2001.

Xie et al., "The Raman detection of peptide tyrosine phosphorylation," *Anal. Biochem.*, 332:116-121, 2004.

Zhang et al., "Raman detection of proteomic analytes," *Anal. Chem.*, 75:5703-5709, 2003.

Zumbusch et al., "Three-Dimensional Vibrational Imaging by Coherent Anti-Stokes Raman Scattering," *Phys. Rev. Lett.*, 82:4142-4145, 1999.

SPATIAL HETERODYNE WIDE-FIELD COHERENT ANTI-STOKES RAMAN SPECTROMICROSCOPY

This patent application claims priority to, and incorporates by reference in its entirety, U.S. Provisional Patent Application Ser. No. 60/729,015 filed on Oct. 21, 2005.

BACKGROUND OF THE INVENTION

1. Field of the Invention

The present invention relates generally to spectroscopy and microscopy. More particularly, embodiments of the present invention provide methods and systems for wide-field coherent anti-Stokes Raman scattering (CARS) microscopy using multiple nonlinear scattering channels to produce multiple, spatially coherent CARS beams from thin samples.

2. Description of Related Art

Optical microscopy has been an indispensable imaging tool in the life and materials sciences for over a century. Unlike electron microscopy, optical techniques offer the potential for studying living systems. Modern microscopes and sophisticated staining techniques routinely provide investigators with views of the workings of cells, both fixed and living. However, a number of researchers and funding organizations have underscored scientific challenges that often exceed the limits of traditional microscopy. For example, there are cellular processes in which fluorescent stains used to distinguish specific functional groups in a cell are either unavailable or undesirable. These extrinsic markers can disrupt normal biochemical processes. As such, imaging contrast based on intrinsic chemical signatures of the molecules under study would be a significant advantage. In addition, high speed or dynamic processes and enhanced spatial resolution are desirable in microscopy.

One approach to functional and chemically-resolved microscopy is to employ vibrational contrast imaging using, for example, Raman emission or infrared absorption. While they do not provide the detailed atomic location obtained in diffraction experiments, vibrational spectroscopies are powerful, for example in the study of biomacromolecules. Raman scattering is of particular interest because it can be excited by visible laser wavelengths, providing significantly greater spatial resolution than infrared microscopy. Vibrational spectra reveal a wealth of information concerning the chemistry, structure, conformation, and interactions of the molecules under study. For example, proteomic analyses, including post-translational modifications such as glycosylation and tyrosine phosphorylation have been measured using Raman scattering. ATP and GTP hydrolysis have been measured spectroscopically by monitoring changes in nucleoside triphosphohydrolase Raman bands.

A principal disadvantage of Raman spectromicroscopy is that Raman scattering is a weak process, typically 10-100 trillion times weaker than emission from efficient fluorophores. A number of groups have experimented with physical and chemical techniques to increase Raman scattering efficiency using, for example, electrodynamic enhancement produced by proximate metal surfaces. Nonlinear vibrational spectroscopies, most notably Coherent Anti-Stokes Raman Scattering (CARS), have been used for many years primarily in the study of combustion processes. Because CARS is generated coherently, the signal strength varies quadratically as the number of molecules excited increases. Signal strengths can be orders of magnitude higher in CARS than in conventional spontaneous Raman scattering.

CARS microscopy typically employs tight focusing of pump and Stokes beams and collinear illumination/collection geometries which facilitate laser wavelength tuning while maintaining the phase-matching condition. Spatial resolution of approximately 300 nm in the lateral direction and approximately 800 nm axially have been reported. Near-IR picosecond lasers are used to reduce autofluorescent background and provide good spectral resolution below 5 $cm^{-1}$, suitable for many condensed systems. Because the anti-Stokes emission is generated coherently, CARS microscopy is significantly faster and more sensitive than conventional Raman microscopy. For example, multiplex CARS microscopy, in which spectrally broad anti-Stokes pulses are stimulated from the sample, has recently been demonstrated. The image acquisition times are roughly sixty times shorter than those in a conventional Raman microscope using identical average power levels and identical samples. Narrow-band CARS microscopy can be up to four orders of magnitude faster than spontaneous Raman microscopy. This also allows investigators to work with significantly lower average power delivered to the sample than would be required in spontaneous Raman, thus reducing potential photo- or thermal damage to fragile specimens.

Scanned microscopy is currently the dominant technique for CARS as well as 3D fluorescence imaging, in part because of the ease of image interpretation and the wide availability of commercial instruments for both linear and multiphoton fluorescence imaging. However, scanned microscopy does not produce sub-wavelength resolution.

Any shortcoming mentioned above is not intended to be exhaustive, but rather is among many that tends to impair the effectiveness of previously known imaging techniques using Raman spectromicroscopy; however, shortcomings mentioned here are sufficient to demonstrate that the methodologies appearing in the art have not been satisfactory and that a significant need exists for the techniques described and claimed in this disclosure.

SUMMARY OF THE INVENTION

In one respect, the disclosure involves wide-field Coherent Anti-Stokes Raman Scattering (CARS) microscopy. The interference of these coherent beams allows for, amongst other things, much higher spatial resolution than can be obtained using conventional imaging techniques. The wide-field Coherent Anti-Stokes Raman Scattering (CARS) microscopy may be extended by using multiple nonlinear scattering channels to produce multiple, spatially coherent CARS beams from thin samples, including for example, samples less than about 1 micron in thickness. Image acquisition in wide-field optical microscopy (having a dimension equal to or greater than about 10 microns) with modulated illumination can be dramatically faster than scanned systems, as well as produce sub-wavelength resolutions. The channels of the present disclosure may interfere in the far-field, allowing enhanced spatial resolution imaging in a manner analogous to that produced in structured illumination fluorescence microscopy. The spatial heterodyne wide-field CARS microscopy allows dynamic, chemically-resolved 3D imaging without extrinsic markers.

The use of the word "a" or "an" is not limited to the singular unless explicitly stated or required in context. The term "coupled" is defined as connected, although not necessarily directly, and not necessarily mechanically.

The term "about," and its variations are defined as being largely but not necessarily wholly what is specified as understood by one of ordinary skill in the art, and in one nonlimiting embodiment the "about" refers to ranges within 10%, preferably within 5%, more preferably within 1%, and most preferably within 0.5% of what is specified.

Embodiments of the disclosure will be better appreciated and understood when considered in conjunction with the following description and the accompanying drawings. It should be understood, however, that the following description, while indicating various embodiments of the disclosure and numerous specific details thereof, is given by way of illustration and not of limitation. Many substitutions, modifications, additions and/or rearrangements may be made.

BRIEF DESCRIPTION OF THE DRAWINGS

The following drawings form part of the present specification and are included to further demonstrate certain aspects of the present disclosure. The figures are examples only. They do not limit the scope of the disclosure.

DESCRIPTION OF ILLUSTRATIVE EMBODIMENTS

Figure 1:
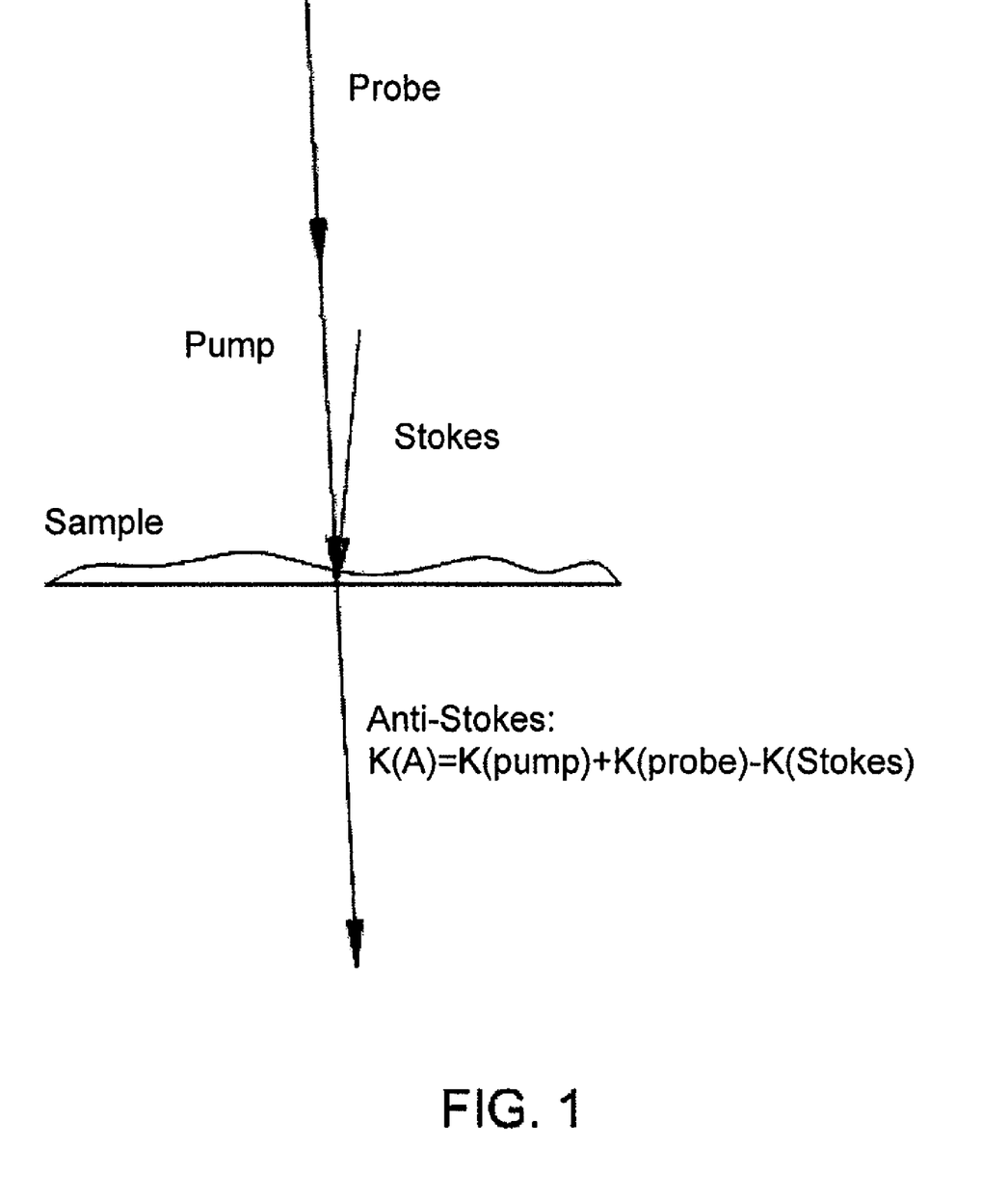
FIG. 1 shows a diagram of pulses of Coherent Anti-Stokes Raman Scattering microscopy, in accordance with an embodiment of the disclosure.

Coherent Anti-Stokes Raman Scattering, or CARS, is an optical process in which high power laser pulses, known as the pump and Stokes beams, may be incident on a sample, and mixed through the third-order nonlinear susceptibility of the medium, as seen in FIG. 1. Qualitatively, these pulses may interfere in the sample to form a transient diffraction grating. A third beam, referred to as a probe beam, scatters from this induced grating and may be Doppler shifted, producing a fourth beam, referred to as an anti-Stokes beam, a coherently generated pulse which is detected. Energy conservation may be determined by the following:

$$\omega_{anti-Stokes} = \omega_{pump} + \omega_{probe} - \omega_{Stokes} \quad \text{Eq. 1}$$

while photon momentum conservation, or phase matching, requires $$k_{anti-Stokes} = k_{pump} + k_{probe} - k_{Stokes} \quad \text{Eq. 2}$$

where $\omega$ and $k$ are the photon's angular frequency and wave vector, respectively. Typically pump and probe pulses are taken from the same high-power laser beam, while the Stokes pulse may be generated in a second source. Vibrational resonances may be excited when $$\omega_{vib} = \omega_{pump} - \omega_{Stokes}, \quad \text{Eq. 3}$$

where $\omega_{vib}$ is a (Raman-active) molecular vibration frequency. Thus, the detected CARS beam may provide a direct measure of vibrational resonances in the sample.

Embodiments of the present disclosure provide for methods for wide-field optical microscopy, particularly spatial heterodyne wide-field CARS microscopy which may allow dynamic, chemically-resolved 3D image of living systems without extrinsic markers. In particular, the present disclosure combines chemically resolved non-linear optical microscopy with wide-field imaging and spatial interference detection to image living systems in 3D. This technique may be used, for example, in biological imaging in a native state without the use of extrinsic markers and may be suitable to a wide variety of applications, including in vivo studies of cell dynamics, neurophysiology studies, and rapid screening of pharmaceuticals. Significant market potential exists for such non-invasive metrology in the pharmaceutical industry as well as in basic science.

To exploit the potential advantages of wide-field light microscopy (e.g., wide-field CARS microscopy), additional information may be extracted from the resulting images. For example, improvements in the spatial resolution of wide field fluorescence microscopy may be achieved by using multiple collection lenses and by employing interference illumination and detection techniques. Structured illumination in fluorescence microscopy may extend resolution to sub-diffraction level by spatial heterodyning. Spatial heterodyning, mixes higher spatial frequencies in the sample back into the region of wave vector space that can be collected by the optical train. By modifying the response in the optical system, structured illumination fluorescence microscopy may be enhanced by a factor of approximately 3.5 over the sub-diffraction level in the axial direction and a factor of approximately 1.4 laterally.

CARS experiments employ pulsed, high peak power lasers. Because CARS is a frequency mixing technique, these experiments may use two temporally coherent laser sources where at least one of these lasers may be tunable. Wide-field CARS microscopy may employ laser sources with higher peak powers than used in scanned systems in the range of micro joules per pulse as opposed to nano joules per pulse. These powers may be obtained, for example, with regeneratively amplified Ti:sapphire (RegA) laser systems combined with tunable pulsed light sources, such as optical parametric amplifiers (OPAs). This system provides enough peak power as well as delivers approximately 100 femtoseconds pulses, which has a bandwidth of approximately 150 cm$^{-1}$. The spectral width may be too broad to perform high-resolution spectroscopy, but is adequate to demonstrate CARS and spatial heterodyne CARS for samples with well-defined Raman bands.

1. Lateral CARS Interference

Figure 2A:
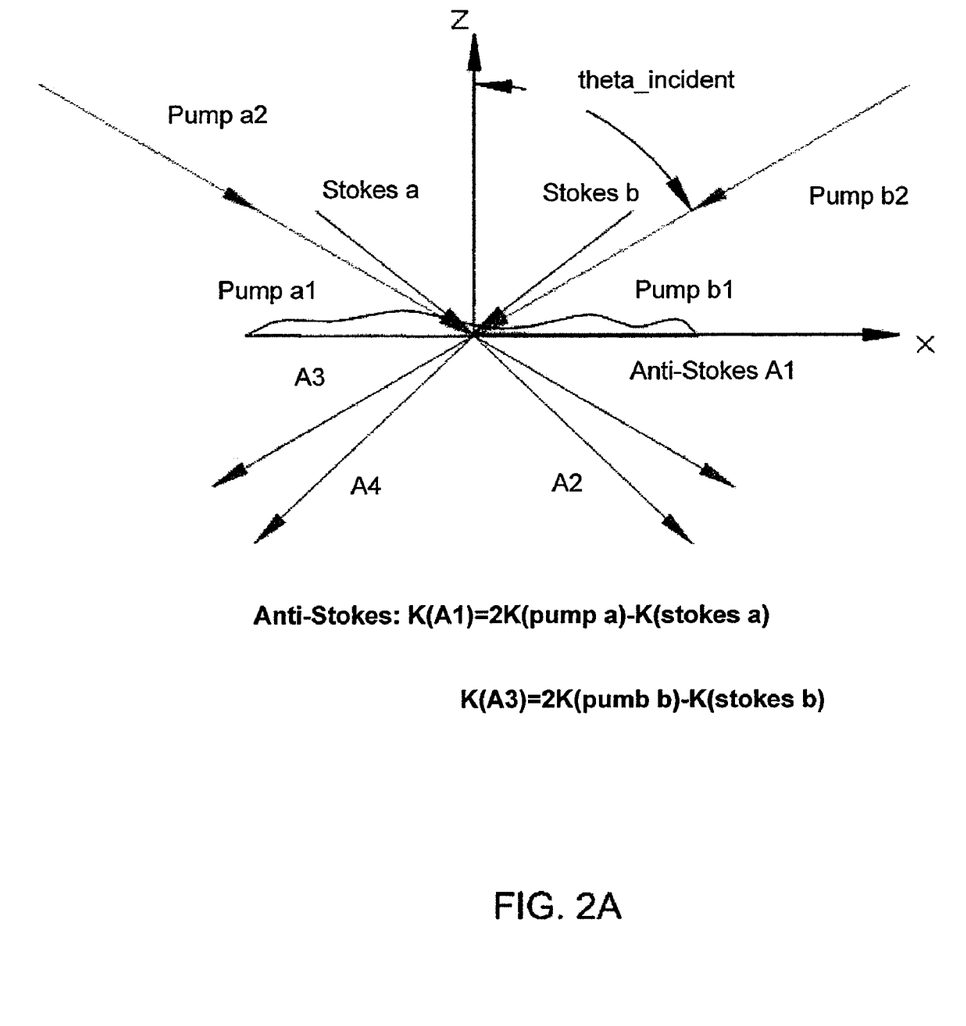
FIG. 2A shows channels of CARS microscopy, in accordance with an embodiment of the disclosure.

In one embodiment, lateral resolution is enhanced. Lateral interference in spatial heterodyne CARS is illustrated in FIG. 2A for the simplified case of two sets of pump and Stokes beams. The pump and Stokes beams may be collinear to facilitate phase matching for a broad range of Raman excitation. In one embodiment, the pump and Stokes beams may be two coherent light beams of different colors, which may illuminate a sample for a duration of a few nanoseconds to a few femtoseconds. The beams shown in FIG. 2A may be slightly misaligned. Possible anti-Stokes channels are labeled A1 through A4. The even numbered anti-Stokes beams, A2 and A4, may be suppressed because of poor phase matching. They may contribute for lower-lying Raman bands. Far-field interference between anti-Stokes beams A1 and A3 may mix a wider range of transverse wave vector components from the sample back into the acceptance range of the optical system. As such, it may be possible to nearly double the transverse spatial resolution in this way.

If these beams were tuned to generate CARS from a spatially uniform sample, the resulting CARS beams may interfere as a result of the phase shifts due to the tilt of the incident wavefronts away from the x-y plane. The field amplitude in the far-field may be modulated in the x-direction, and may have the form $$E_{AS}(k) \sim \delta(k-k_{anti\text{-}Stokes\_a}) + \delta(k-k_{anti\text{-}Stokes\_b}) \quad \text{Eq. 4.}$$

The anti-Stokes intensity in this case may be a standing wave with pitch $$d_A = \frac{1}{2}\frac{2\pi}{k_{A(trans)}}, \quad \text{Eq. 5}$$

where $$k_{A(trans)} = 2k_{anti\text{-}Stokes}\sin\theta_{incident} \quad \text{Eq. 6}$$

$$k_{anti\text{-}Stokes} = 2\pi/\lambda_{anti\text{-}Stokes} \quad \text{Eq. 7}$$

and $\lambda_{anti\text{-}Stokes}$ is the anti-Stokes wavelength. This may be an effect when imaging interference from coherent sources, and the pitch of the resulting interference pattern may be smaller than the wavelength of light.

In one respect, suppose the uniform sample is replaced with a 1-D grating capable of producing CARS with spacing $d_S$, wave vector $k_S=2\pi/d_S$ in the x-direction. If $k_S$ is greater than $k_{Max}$, where $k_{Max}$ is the magnitude of the largest wave vector that can be transmitted by the optical system, the sample features would not be resolvable using conventional techniques. The resolution criterion is usually expressed in terms of the minimum resolvable feature size known as a Rayleigh limit, $d_{min}=0.61\lambda/NA$, where NA is the numerical aperture. Features closer than $d_{min}$ cannot be resolved by conventional optical microscopy.

However, the interference produced by the two non-collinear illumination paths may serve to fold the Fourier components of the sample density. More precisely, its nonlinear susceptibility, $\chi^{(3)}$ in the case of CARS imaging back into the range of wave vectors that may be collected by the optical system. A "beat" pattern is obtained in the far field, whose pitch is $$d(\text{spatial\_heterodyne}) = \frac{2\pi}{|2k_{A(trans)} - k_S|}. \quad \text{Eq. 8}$$

Figure 3A:
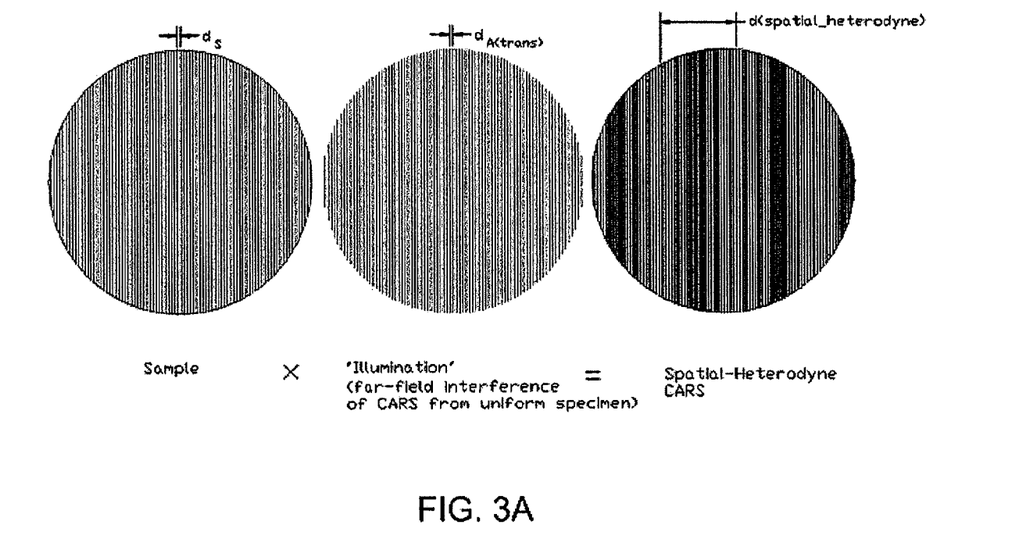
FIG. 3A shows a real-space illustration of spatial heterodyne CARS, in accordance with an embodiment of the disclosure. Fine real-space features illuminated by multiple incident CARS paths should produce a coarser grid (moiré pattern) of CARS scattering, which can be imaged by the optical system.
Figure 3B:
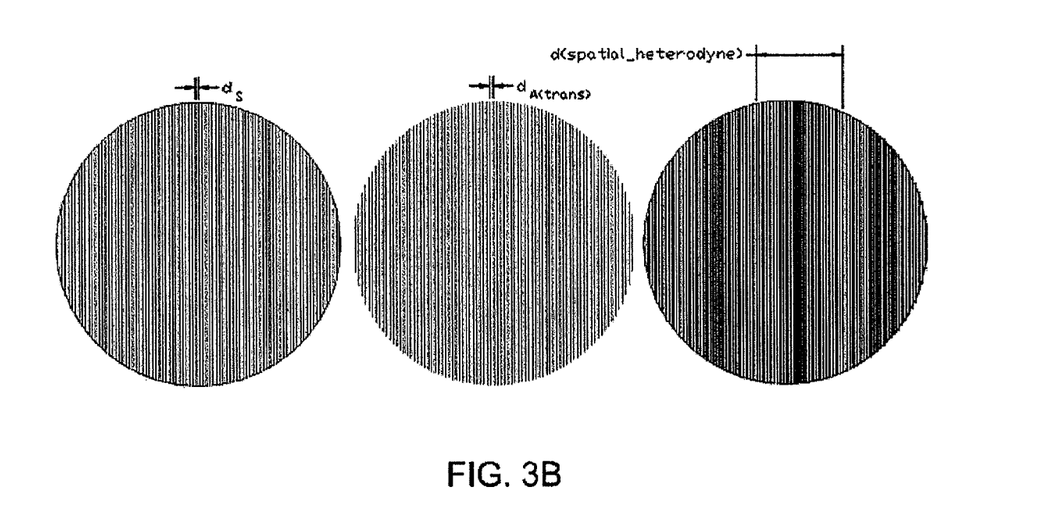
FIG. 3B shows a shift in the spatial heterodyne pattern of FIG. 3A when the sample is shifted to the right by $d_s/2$.

The result is similar to the moiré effect shown in FIGS. 3A and 3B. The lateral spatial resolution may be doubled in this way.

Further, the registration of the sample in this example may be determined by adjusting the phase of the illumination pattern, such as by varying the length of one illumination path relative to the other or by translating the sample. Referring to FIG. 3B, the effect in the spatial-heterodyne pattern when the sample is shifted to the right by $d_S/2$ is shown. Note that the resulting moiré pattern is roughly 180° out of phase with that in FIG. 3A.

To illustrate the improvement in resolution that is associated with such an imaging system, a sample rich in aromatic C—H bonds with a frequency of approximately 3054 cm$^{-1}$ using pump and Stokes beams with wavelengths 855 nm and 1.157 µm, respectively is imaged. In this example, the anti-Stokes emission is about 678 nm and the lateral full width half maximum of the resulting images is about 307 nm. Images were obtained using oil immersion lenses with a numerical aperture (NA) of approximately 1.4. As illustrated in FIG. 2A, lateral resolution of approximately 145 nm for aqueous samples are achievable. It is noted that this is nearly six times smaller than the pump laser wavelength.

Figure 2B:
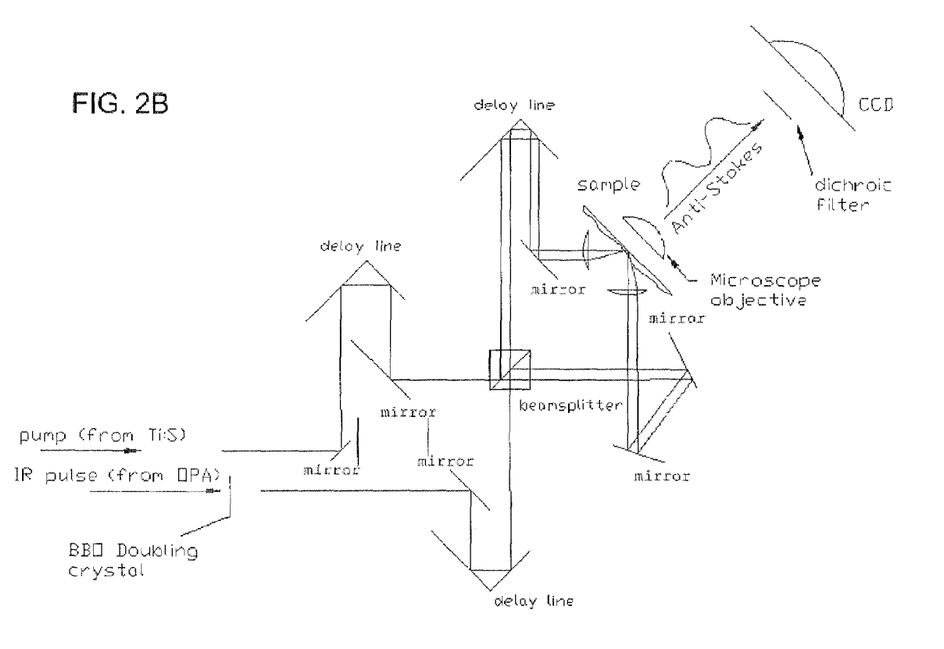
FIG. 2B shows an experimental arrangement to demonstrate lateral interference in CARS microscopy, in accordance with an embodiment of the disclosure.

In one embodiment, lateral interference of CARS from thin samples may be generated using an optical layout such as, for example, the system illustrated in FIG. 2B. In one respect, the laser beams may be incident on samples at 45° to the sample normal. A delay line may be used to ensure that the pump and Stokes pulses overlap at the sample. The path length of one illumination source may be adjusted by a linear translation stage to allow pulse overlap and CARS interference. Initially, the delay line may be adjusted to produce CARS from each incident illuminating path while blocking the other in turn. CARS signals may be detected using a CCD camera. Next, the sample may be illuminated with both sets of laser beams and the resulting interference pattern may be measured.

A similar axial moiré effect may be exploited to achieve an even more dramatic resolution increase in this direction. As in the previous example, higher Fourier components of the sample's nonlinear susceptibility, corresponding to finer spatial features may be retrieved by the optical system by mixing these with multiple illumination beams. In this case, the incident laser beams may counter propagate axially, requiring two microscope objectives. These may also used to collect CARS emission efficiently from both faces of the sample.

2. Spatial Heterodyne CARS

Similar to the lateral setup, spatial heterodyning in CARS microscopy may be demonstrated by measuring the spacing of moiré fringes generated from a patterned sample using an imaging set-up, such as the system shown in FIG. 2B. In one embodiment, a series of 1-D gratings in thin photoresist films may be generated by exposing the photoresist in a two beam interference pattern using a UV laser. The pitch of these gratings may be measured directly using atomic force microscopy. For example, using a 0.85 numerical aperture (NA) objective lens to image CARS from the C—H Raman bands in the sample with an anti-Stokes wavelength of approximately 645 nm, features as small as about $\lambda_A/3$, approximately 215 nm, may be observed.

In one embodiment, a Ti:S laser may produce pulses of about 800 nm wavelength. These pulses may be used as the pump photons for CARS generation. Stokes photons with wavelengths from approximately 870 nm to approximately 1060 nm may be generated by a tunable source such as, but not limited to, an optical parametric amplifier (OPA). As such, CARS imaging of samples may be performed with Raman bands ranging from approximately 1000 cm$^{-1}$ to approximately 3050 cm$^{-1}$. This range will yield anti-Stokes scattering with wavelengths from about 643 nm to about 741 nm, respectively. Wavelengths of pump and Stokes beams may be checked using a wavemeter, which could be used for the initial set-up.

3. Axial Interference in CARS Microscopy

Figure 4A:
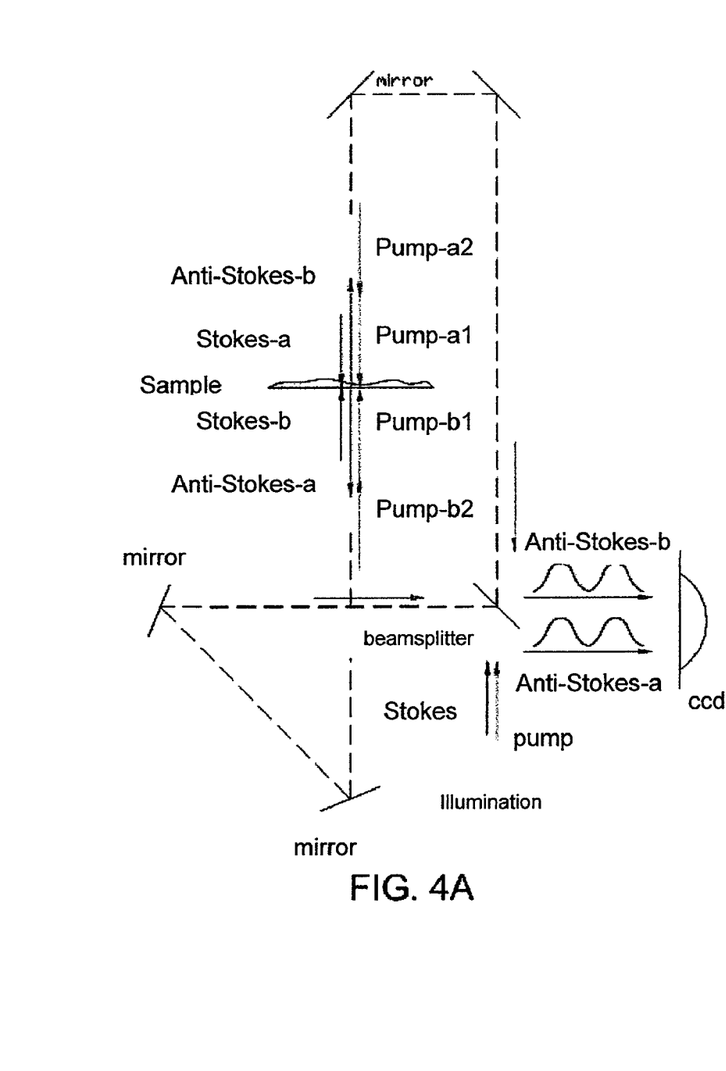
FIGS. 4A and 4B show a schematic illustration of a multi-beam approach for increasing axial resolution in widefield CARS microscopy, in accordance with an embodiment of the disclosure.
Figure 4B:
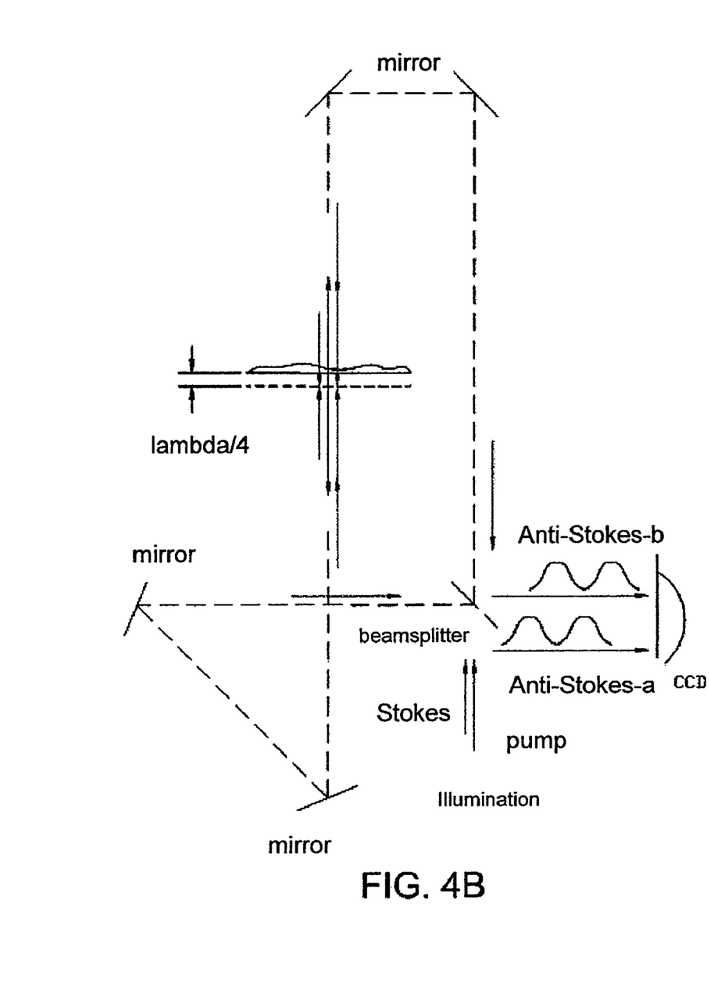
Figure 6:
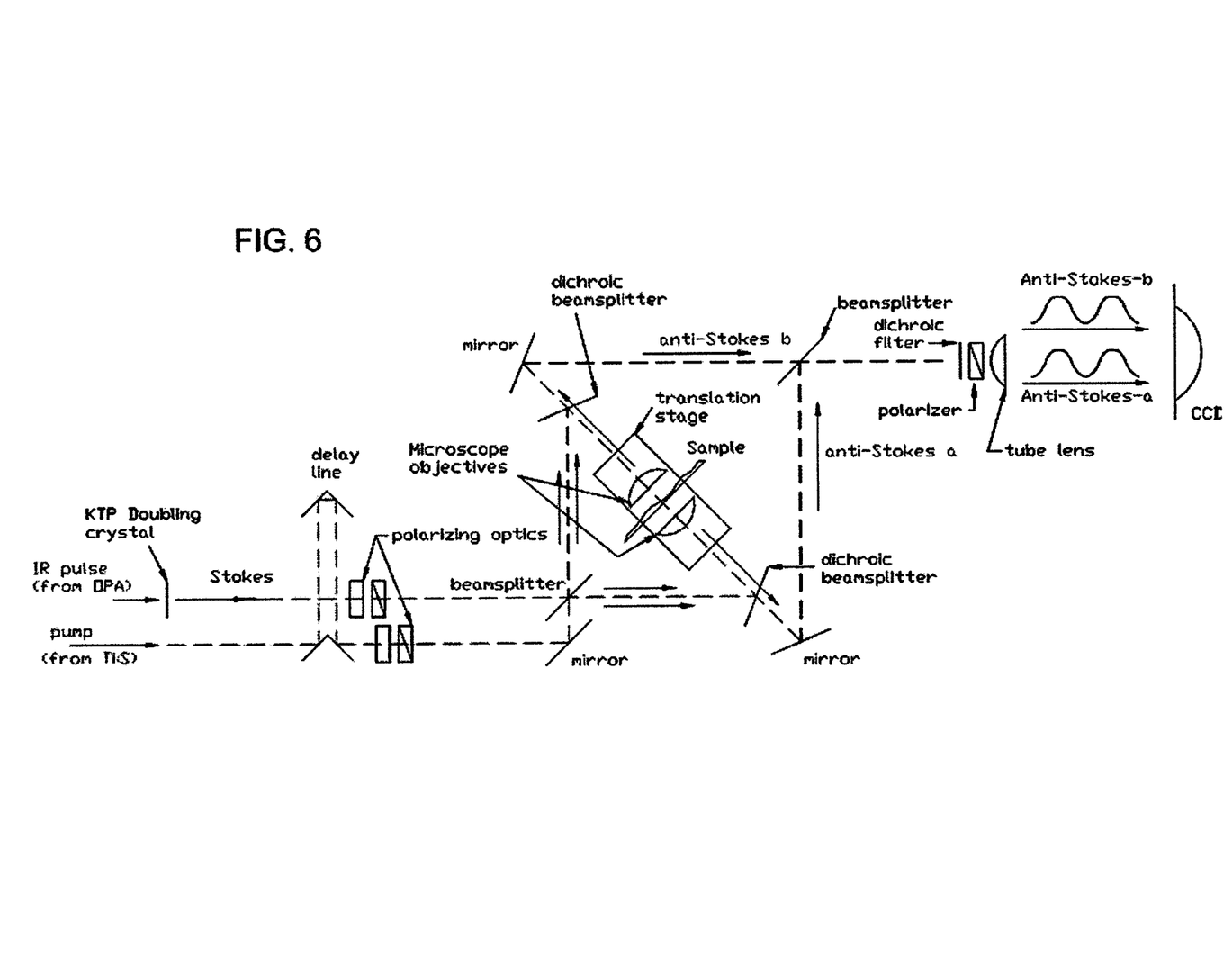
FIG. 6 shows a setup for demonstrating axial interference in CARS microscopy, in accordance with an embodiment of the disclosure.

Axial interference may be determined by generating CARS in two counter propagating directions from the sample. A schematic illustration of an experimental set up is shown in FIG. 4A, 4B, or 6. The setup shown may provide independent optimization of the phases in the beam paths. In one embodiment, the sample position may be adjusted as described below to allow an overlap of the CARS images at the CCD detector.

In one embodiment, a thin sample including a polymer or dye film may be placed between two glass cover slips and may be held on a translation stage driven by a stepping motor and placed at the focus of two microscope objectives. Using a pair of high numerical aperture (NA) microscope objectives (as shown, for example, in FIG. 6), the CARS interference may be observed when the lengths of the two paths from the sample to the detector differ by less than a coherence length. For example, a pair of 45×0.65 NA lenses and a pair of 50×0.85 NA lenses may be used where one microscope objective may be fixed in position, while the second may be mounted on a three-axis positioner. The focusing of the lenses may be done by adjusting the positions of the sample and movable objective relative to the fixed objective. The lenses, sample, and their positioners may be mounted on a computer-controlled linear translation stage. This stage may move to allow interference of the counter propagating CARS beams leaving the sample.

CARS interference may be observed when the lengths of the two paths from the sample to the detector differ by less than a coherence length. Depending on the temporal length of the laser pulses used, which may be approximately 100 fs to 3 ps, the temporal length may range from approximately 30 μm to approximately 1 mm.

Precise, confocal alignment of the microscope objectives is critical for axial interference CARS. In one embodiment, collimated beams from a Ti:S laser through the optical train in the absence of a sample may be propagated. The mirrors and lens position may be adjusted so that the beams are overlapped in the illumination ring. Similar alignment may be done with beams from the OPA. Condenser lenses (not shown) may be installed to focus beams from the Ti:S and OPA at the back conjugate plane of each objective lens so that a wide-field illumination is produced at the sample.

The condenser lens may subsequently be removed temporarily to perform preliminary axial position alignment of the sample stage. Fluorescent dye samples such as, but not limited to coumarin in ethanol or fluorescein in NaOH at the objective focus may be added. Coumarin fluorescence or fluorescein fluorescence strong enough to be seen by the unaided eye may be produced by two-photon excitation from the Ti:S laser and OPA, respectively. In one embodiment, coumarin fluorescence (in blue) and flourescein fluorescence (in green) are used. Fine focusing may be performed to ensure that the fluorescence beams are collimated and co-propagating in the image ring of the apparatus. Next, attenuation of the incident beam and scanning of the translation stage to locate the peak in fluorescence yield may be performed. This step may occur when the sample is at the point at which the counter propagating illumination pulses coincide. In effect, the sample may be used as an auto-correlator. Additional linear adjustments may be placed on one dichroic beam splitter in the illumination ring and one mirror in the image ring to optimize the phase of the illumination and CARS pulses, respectively, within these beam paths. The tube lens position may be adjusted to focus the fluorescence image on the sample. The condenser lenses may then be re-inserted.

Next, the spatial resolution of the wide-field CARS microscope may be analyzed. To determine the spatial resolution, a 0.1 μm polystyrene microsphere may be used as a point source and stepped through the focus to determine the point spread function of the imaging system. The Fourier transform of the optical transfer function may determine the range of wave vectors admitted by the microscope. Both the horizontal and axial resolution may be obtained from the optical transfer function. Next, the thin polystyrene and PMMA film samples may be scanned through the focus to estimate the axial sectioning ability of the microscope. The phase of the illuminating beams may be systematically varied by changing the delay line length and the illumination ring spacing. This may allow for the effect of illumination interference on image formation in this wide-field CARS microscope to be measured.

4. Axial Resolution in CARS Spectroscopy

An experimental arrangement to demonstrate enhanced axial resolution in CARS microscopy is shown schematically in FIGS. 4A and 4B. In one respect, the sample may be placed between high-NA objectives (not shown). Collinear pump and Stokes beams may be incident from opposite sides and may be unfocused with approximately tens of micrometer spot sizes at the sample. CARS beams may be stimulated in the forward direction and may be collected by the objective lenses. Both images interfere at the detector. Referring to FIGS. 4A and 4B, the intensity at the detector varies from maximum constructive interference of the CARS beams to minimum destructive interference as the sample is displaced axially by ¼ of the anti-Stokes wavelength. The handedness of an image produced by one objective is the reverse of that from the other, so an odd number of reflections may be needed to superimpose the images.

Resolution enhancement in the scheme illustrated in FIGS. 4A and 4B may be understood in terms of the analysis for patterned illumination in fluorescence microscopy, although an accurate model for spatial heterodyne CARS may require a more sophisticated analysis. A spatial Fourier transformed electric field for CARS generated by the sample may be given by the convolution $$E(k) = \rho(k) \otimes A_{AS}(k) \qquad \text{Eq. 9}$$

where k is the wavevector, $\rho(k)$ is the E-field intensity for light at wavevector $k_A$ that is accepted by the optical system, namely a spherical shell of radius $k_A$ that is truncated by the finite angular acceptance of the lenses, and $A_{AS}$ is the Fourier transform of the spatial interference:

$$A_{AS}(k) \sim \delta(k - k_{anti\text{-}Stokes\_a}) + \delta(k - k_{anti\text{-}Stokes\_b}) \qquad \text{Eq. 10}$$

Figure 5:
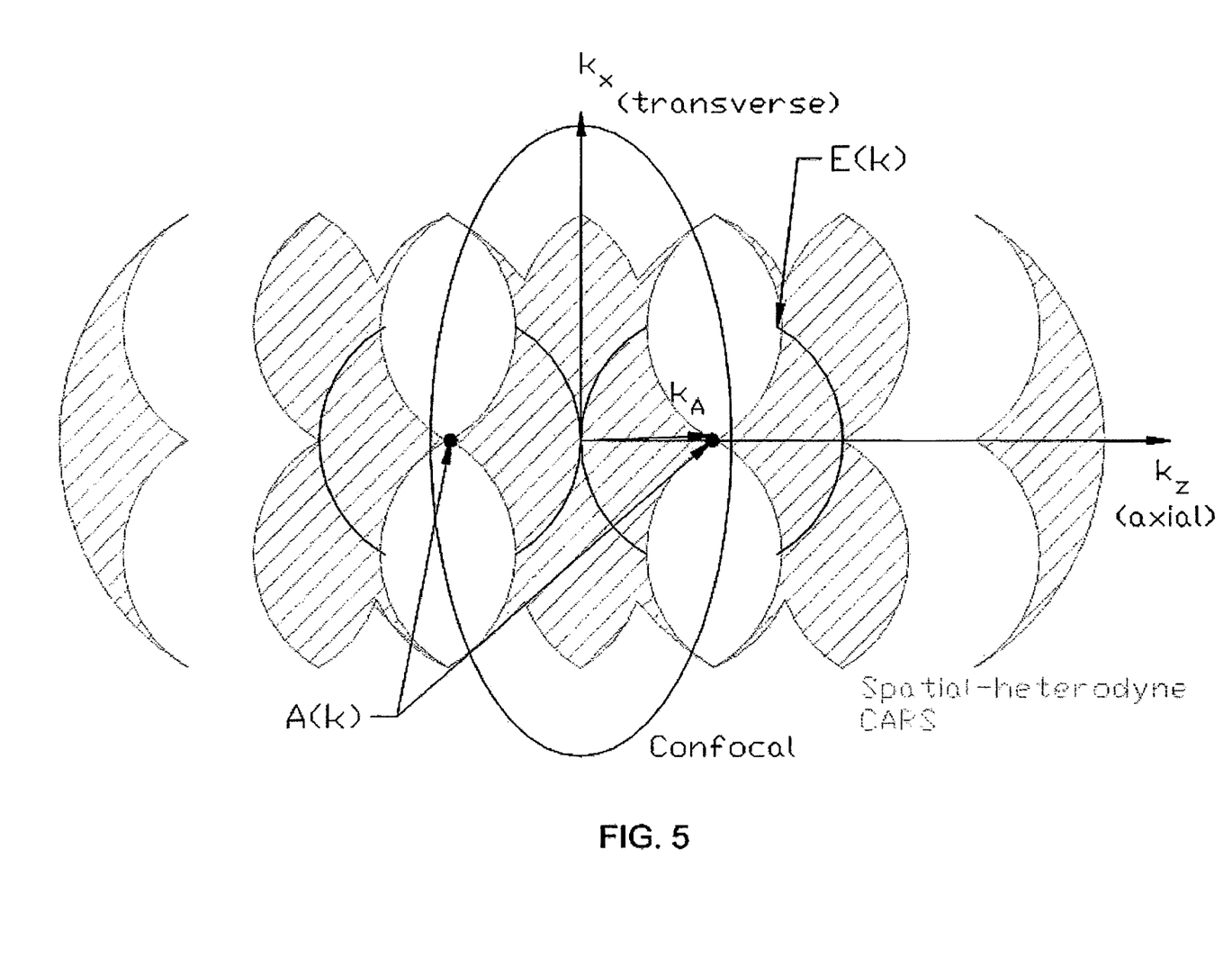
FIG. 5 shows a 2D cross-section of an effective optical transfer function (OTF) support showing the principle of axial resolution enhancement in wide-field spatial-heterodyne CARS, in accordance with an embodiment of the disclosure.

The Fourier transformed intensity is the autocorrelation of E(k). For a localized delta-function CARS source, this autocorrelation may be related to the nonlinear optics generalization of the system optical transfer function (OTF) support. A 2D projection of this is shown qualitatively in FIG. 5 for a two-objective system with NA of approximately 1.3. In one embodiment, larger accessible wave vectors correspond to smaller resolvable spatial features. Image reconstruction in such a system may require varying the optical path lengths, as in an interferometer, to determine the phase of the CARS field. The analogous problem may be encountered in structured illumination fluorescence microscopy. As in standing wave microscopy, there may be gaps in the OTF support in this case which stems from the fringe ambiguity of the anti-Stokes interference. By superimposing pump and Stokes beams with transverse wave vector components, it should be possible to remove these OTF gaps and increase the lateral resolution of spatial heterodyne CARS.

5. Higher Resolution CARS Spectroscopy

Spectral compression optics including gratings and slit assemblies may be added to reduce the bandwidth of the pump and Stokes laser pulses to approximately 5 cm$^{-1}$. As such, higher resolution measurements of signature spectral bands of drug samples may be analyzed and compare to those of spontaneous Raman spectra of the same compounds.

Wide-field CARS microscopy can greatly impact the health care and the life sciences industries. For example, pharmaceutical companies spend millions of dollars evaluating each potential drug through animal and clinical studies. The lack of detailed understanding of how these potential agents work at the cellular level is one of the biggest handicaps today in evaluating each potential drug and determining which are safe and efficacious. A method to rapidly assess the pharmacokinetics of a new drug candidate in terms of its specific biochemical and physiological activity at the cellular level would significantly reduce this handicap and allow major reductions in the cost and time to evaluate a potential new drug. Wide field spatial heterodyne CARS microscopy could provide cell-based, label-free, in vitro pharmacokinetic assays for the pharmaceutical industry, potentially saving billions of dollars in drug development costs.

With the benefit of the present disclosure, those having ordinary skill in the art will comprehend that techniques claimed herein may be modified and applied to a number of additional, different applications, achieving the same or a similar result. The claims cover all such modifications that fall within the scope and spirit of this disclosure.

REFERENCES

Each of the following references is hereby incorporated by reference in its entirety:
U.S. Pat. No. 4,405,237
U.S. Pat. No. 5,671,085
U.S. Pat. No. 6,798,507
Cheng and Xie, *J. Phys. Chem.*, B108:827-840, 2004.
Duncan et al., *Opt. Lett.*, 7:350-352, 1982.
Frohn et al., *Proc. Natl. Acad. Sci. USA*, 97:7232-7236, 2000.
Gustaffson et al., *J. Microscopy*, 195:10-16, 1999.
Heinrich et al., *App. Phys. Lett.*, 94:816, 818, 2004.
Holtom et al., *Traffic*, 2:781-788, 2001.
Jenkins et al., *Biospectroscopy*, 5:3-8, 1999.
Kee and Cicerone, *Opt. Lett.*, 29:2701-2703, 2004.
Levenson, In: *Introduction to Nonlinear Laser Spectroscopy*, NY, Academic Press, 1982.
Minsky, *Scanning*, 10:128-138, 1988.
Potma et al., *Proc. Natl. Acad. Sci. USA*, 98:1577-1582, 2001.
Xie et al., *Anal. Biochem.*, 332:116-121, 2004.
Zhang et al., *Anal. Chem.*, 75:5703-5709, 2003.
Zumbusch et al., *Phys. Rev. Lett.*, 82:4142-4145, 1999.

What is claimed is:

1. A method, comprising:
   directing radiation having a first wavelength and a second wavelength to a sample;
   producing a plurality of simultaneous anti-Stokes beams from a plurality of channels from the first and second wavelengths; and
   generating an image from an interference of the plurality of anti-Stokes beams.

2. The method of claim 1, the step of directing radiation comprising directing radiation from a Ti:sapphire laser.

3. The method of claim 1, the step of directing radiation comprising directing the radiation collinearly on the sample.

4. The method of claim 1, the plurality of channels comprising a plurality of non-linear scattering channels.

5. The method of claim 1, the plurality of anti-Stokes beams comprising a plurality of spatially coherent anti-Stokes Raman scattering (CARS) beams.

6. The method of claim 5, the plurality of anti-Stokes beams having a dimension greater than about 10 microns.

7. The method of claim 1, the radiation comprising a first and second coherent light beam of different colors.

8. The method of claim 1, the first wavelength and second wavelength comprising tunable wavelengths.

9. The method of claim 1, where the first wavelength is different than the second wavelength.

10. The method of claim 9, where a difference between the first wavelength and the second wavelength to be resonant with one or more molecular vibrational energy levels of the sample.

11. The method of claim 10, further comprising generating coherent anti-Stokes Raman scattering in the sample.

12. The method of claim 11, further comprising collecting the generated coherent anti-Stokes Raman scattering.

13. The method of claim 12, the step of collecting comprising collecting the coherent anti-Stokes Raman scattering using one or more lenses.

14. The method of claim 12, further comprising projecting the collected coherent anti-Stokes Raman scattering onto an array detector.

15. A method comprising:
   providing a sample;
   illuminating the sample with radiation having at least one wavelength;
   generating a coherent anti-Stokes Raman scattering (CARS) interference from a plurality of numerical aperture microscope objectives from the at least one wavelength wherein the sample is positioned between at least two of the plurality of numerical aperture microscope objectives; and
   generating an image from the CARS interference.

16. The method of claim 15, where the step of generating the interference comprises focusing the numerical aperture microscope objectives.

17. The method of claim 16, the step of illuminating the sample comprising illuminating the sample with a Ti: sapphire laser.

* * * * *